US00PP36902P2

(12) United States Plant Patent
Moseley

(10) Patent No.: US PP36,902 P2
(45) Date of Patent: Aug. 26, 2025

(54) ***PETUNIA* PLANT NAMED 'WGPETSMVPV25'**

(50) Latin Name: *Petunia X hybrida*
Varietal Denomination: WGPETSMVPV25

(71) Applicant: Adam Moseley, Kyle, TX (US)

(72) Inventor: Adam Moseley, Kyle, TX (US)

(73) Assignee: WINGEN, LLC, Mustang Ridge, TX (US)

( * ) Notice: Subject to any disclaimer, the term of this patent is extended or adjusted under 35 U.S.C. 154(b) by 0 days.

(21) Appl. No.: 18/755,560

(22) Filed: Jun. 26, 2024

(51) Int. Cl.
*A01H 5/02* (2018.01)
*A01H 6/82* (2018.01)

(52) U.S. Cl.
USPC ..... Plt./356.17

(58) Field of Classification Search
USPC ..... Plt./356.17
CPC . A01H 5/02; A01H 5/00; A01H 6/824; A01H 6/82
See application file for complete search history.

(56) References Cited

U.S. PATENT DOCUMENTS

PP16,144 P2 * 12/2005 Lander ..... Plt./356.18

* cited by examiner

*Primary Examiner* — June Hwu
(74) *Attorney, Agent, or Firm* — C. Anne Whealy

(57) ABSTRACT

A new and distinct *Petunia* plant named 'WGPETSMVPV25', characterized by its upright to outwardly spreading and mounding to eventually trailing and decumbent plant habit; vigorous growth habit and rapid growth rate; freely branching habit; dense and bushy plant form; early and freely flowering habit; single-type flowers that are reddish purple in color with purplish red to dark purple-colored venation and dark purple-colored throats; and excellent container and garden performance.

2 Drawing Sheets

Figure 1:
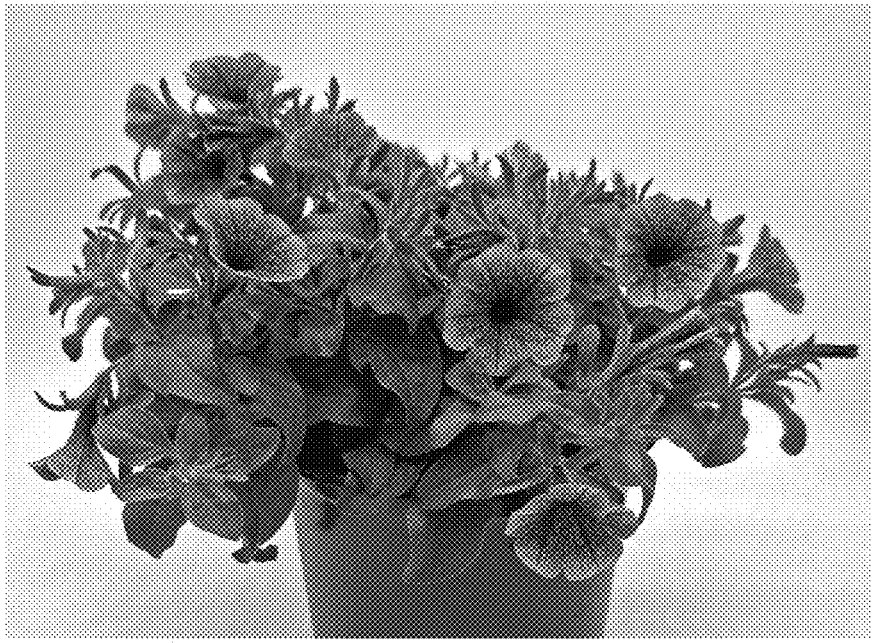

Botanical designation: *Petunia* X *hybrida*.
Cultivar denomination: 'WGPETSMVPV25'.

BACKGROUND OF THE INVENTION

The present invention relates to a new and distinct cultivar of Petunia plant, botanically known as *Petunia* X *hybrida* and hereinafter referred to by the name 'WGPETSMVPV25'.

The new Petunia plant is a product of a planned breeding program conducted by the Inventor in Alajuela, Costa Rica and Mustang Ridge, Texas. The objective of the breeding program is to create new vigorous, freely-branching and uniformly mounding Petunia plants with early and freely flowering habit, attractive flowers and good garden performance.

The new Petunia plant originated from a cross-pollination made by the Inventor on Jun. 16, 2020 in Alajuela, Costa Rica of *Petunia* X *hybrida* 'USTUNJ1901', disclosed in U.S. Plant Pat. No. 28,051, as the female, or seed, parent with *Petunia* X *hybrida* 'BBTUN93201', disclosed in U.S. Plant Pat. No. 33,278, as the male, or pollen, parent. The new Petunia plant was discovered and selected by the Inventor as a single flowering plant within the progeny of the stated cross-pollination in a controlled greenhouse environment in Mustang Ridge, Texas on Sep. 21, 2021.

Asexual reproduction of the new Petunia plant by vegetative terminal cuttings in a controlled greenhouse environment in Mustang Ridge, Texas since Oct. 10, 2021 has shown that the unique features of this new Petunia plant are stable and reproduced true to type in successive generations.

SUMMARY OF THE INVENTION

Plants of the new Petunia have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'WGPETSMVPV25'. These characteristics in combination distinguish 'WGPETSMVPV25' as a new and distinct Petunia plant:

1. Upright to outwardly spreading and mounding to eventually trailing and decumbent plant habit.
2. Vigorous growth habit and rapid growth rate.
3. Freely branching habit; dense and bushy plant form.
4. Early and freely flowering habit.
5. Single-type flowers that are reddish purple in color with purplish red to dark purple-colored venation and dark purple-colored throats.
6. Excellent container and garden performance.

Plants of the new Petunia can be compared to plants of the female parent, 'USTUNJ1901'. In side-by-side comparisons, plants of the new Petunia differ primarily from plants of 'USTUNJ1901' in flower color as plants of the new Petunia have flowers that are reddish purple in color with purplish red to dark purple-colored venation and dark purple-colored throats whereas flowers of plants of 'USTUNJ1901' are white in color with a distinct and stable bluish violet star-shaped color pattern.

Plants of the new Petunia can be compared to plants of the male parent, 'BBTUN93201'. In side-by-side comparisons, plants of the new Petunia differ primarily from plants of 'BBTUN93201' in flower color as plants of the new Petunia have flowers that are reddish purple in color with purplish red to dark purple-colored venation and dark purple-colored throats whereas flowers of plants of 'BBTUN93201' are purple in color. In addition, flowers of plants of the new Petunia resist fading with subsequent development whereas flowers of plants of 'BBTUN93201' readily fade with subsequent development.

Plants of the new Petunia can be compared to plants of *Petunia* X *hybrida* 'USTUN2401M', disclosed in U.S. Plant Pat. No. 29,664. In side-by-side comparisons, plants of the new Petunia differ primarily from plants of 'USTUN2401M' in the following characteristics:

1. Plants of the new Petunia are more compact than plants of 'USTUN2401M'.
2. Plants of the new Petunia have smaller flowers than plants of 'USTUN2401M'
3. Flowers of plants of the new Petunia are reddish purple in color with purplish red to dark purple-colored venation and dark purple-colored throats whereas flowers of plants of 'USTUN2401M' are hot pink in color.

Plants of the new Petunia can also be compared to plants of *Petunia* X *hybrida* 'Lanbor', disclosed in U.S. Plant Pat. No. 16,144. In side-by-side comparisons, plants of the new Petunia differ primarily from plants of 'Lanbor' in the following characteristics:

1. Plants of the new Petunia are more compact than and not as vigorous as plants of 'Lanbor'.
2. Plants of the new Petunia are denser than and not as open as plants of 'Lanbor'.
3. Plants of the new Petunia have smaller flowers than plants of 'Lanbor'.
4. Flowers of plants of the new Petunia are reddish purple in color with purplish red to dark purple-colored venation and dark purple-colored throats whereas flowers of plants of 'Lanbor' are light purple in color with dark purple-colored centers.

BRIEF DESCRIPTION OF THE PHOTOGRAPHS

The accompanying colored photographs illustrate the overall appearance of the new Petunia plant showing the colors as true as it is reasonably possible to obtain in colored reproductions of this type. Colors in the photographs may differ slightly from the color values cited in the detailed botanical description which accurately describe the colors of the new Petunia plant.

The photograph on the first sheet (FIG. 1) is a side perspective view of a typical flowering plant of 'WGPETSMVPV25' grown in a container.

Figure 2:
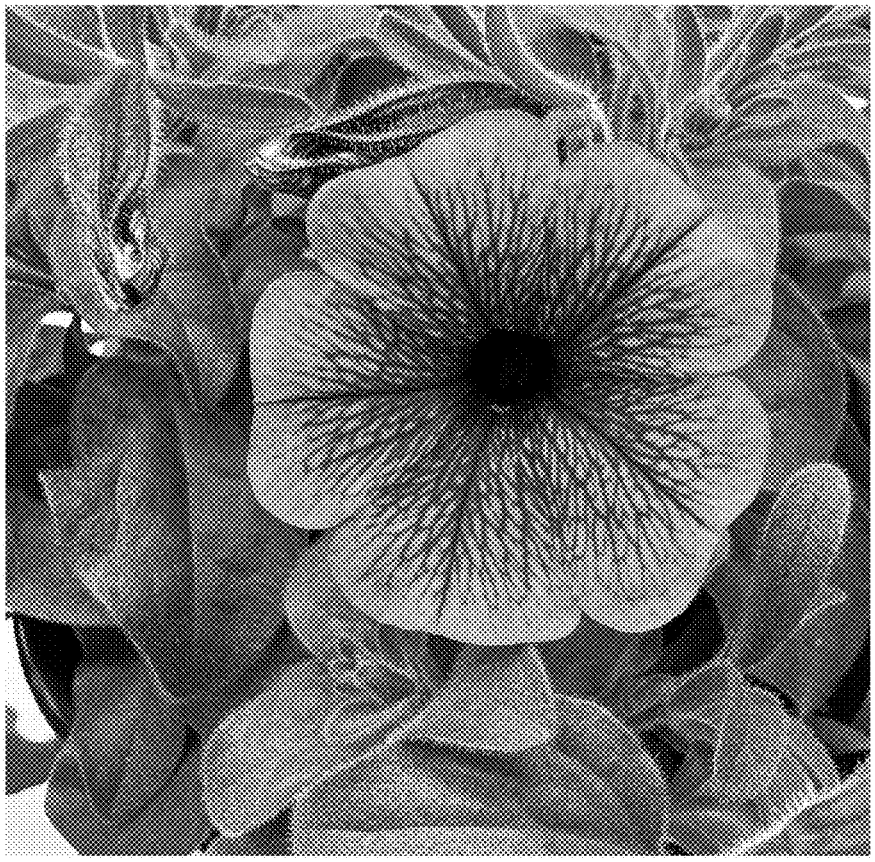

The photograph on the second sheet (FIG. 2) is a close-up view of a typical flowering plant of 'WGPETSMVPV25'.

DETAILED BOTANICAL DESCRIPTION

The aforementioned photographs and following observations and measurements describe plants grown during the late winter and early spring in 10.75-cm containers in a glass-covered greenhouse in Loudon, New Hampshire and under cultural practices typical of commercial Petunia production. During the production of the plants, day and night temperatures averaged 20° C. Plants were seven weeks from planting rooted cuttings when the photographs and description were taken. In the following description, color references are made to The Royal Horticultural Society Colour Chart, 2015 Edition, except where general terms of ordinary dictionary significance are used.

Botanical classification: *Petunia* X *hybrida* 'WGPETSMVPV25'.

Parentage:

*Female, or seed, parent.*—*Petunia* X *hybrida* 'USTUNJ1901', disclosed in U.S. Plant Pat. No. 28,051.

*Male, or pollen, parent.*—*Petunia* X *hybrida* 'BBTUN93201', disclosed in U.S. Plant Pat. No. 33,278.

Propagation:

*Type.*—Terminal vegetative cuttings.

*Time to initiate roots, summer.*—About three to four days at ambient temperatures about 28° C.

*Time to initiate roots, winter.*—About five to seven days at ambient temperatures about 20° C.

*Time to produce a rooted plant, summer.*—About three or four weeks at ambient temperatures about 28° C.

*Time to produce a rooted plant, winter.*—About four to five weeks at ambient temperatures about 20° C.

*Root description.*—Fine, fibrous; typically white in color, actual color of the roots is dependent on substrate composition, water quality, fertilizer type and formulation, substrate temperature and physiological age of roots.

*Rooting habit.*—Freely branching; medium density.

Plant description:

*Plant and growth habit.*—Upright to outwardly spreading and mounding to eventually trailing and decumbent plant habit; freely branching habit with about three to five primary lateral branches with secondary laterals developing potentially at every node, dense and bushy plant form; pinching enhances development of lateral branches; vigorous growth habit and rapid growth rate.

*Plant height.*—About 14 cm to 16 cm.

*Plant diameter* (*area of spread*).—About 35 cm to 40 cm.

*Lateral branches.*—Length: About 18 cm to 20 cm. Diameter: About 3 mm. Internode length: About 1.2 cm to 1.5 cm. Strength: Strong; flexible, not brittle. Aspect: Initially upright then outwardly spreading to trailing and decumbent. Texture and luster: Densely pubescent; pubescence, fine; moderately glossy. Color, developing and developed: Close to 146A; on surfaces directly exposed to sunlight, variably tinged with close to N79A.

Leaf description:

*Arrangement.*—Alternate before flowering; opposite after flowers develop; leaves simple.

*Length.*—About 5.2 cm.

*Width.*—About 3.5 cm.

*Shape.*—Broadly ovate.

*Apex.*—Rounded acute.

*Base.*—Cuneate, rounded.

*Margin.*—Entire, slightly to moderately undulate.

*Texture and luster, upper and lower surfaces.*—Moderately pubescent, pubescence, minute; slightly glossy.

*Venation pattern.*—Pinnate, arcuate.

*Color.*—Developing leaves, upper and lower surfaces: Close to 146A. Fully developed leaves, upper surface: More green than 146A; venation, close to 146A. Fully developed leaves, lower surface: Close to 146B; venation, close to 144B.

*Petioles*.—Length: About 1.2 cm. Diameter: About 3 mm. Strength: Moderately strong, flexible. Texture and luster, upper and lower surfaces: Moderately pubescent; slightly glossy. Color, upper and lower surfaces: Close to 144A.

Flower description:

*Flower type and flowering habit*.—Single terminal and axillary salverform flowers; flowers face mostly upward to outwardly; freely flowering habit with about 92 developing flowers and open flowers per plant.

*Natural flowering season*.—Long day responsive; long flowering period, plants flower from early spring until frost in the autumn, flowering continuous during this period; early flowering habit, depending on temperature, plants begin flowering about four to six weeks after planting rooted young plants.

*Flower longevity on the plant*.—Depending on temperature, about one to two weeks; petals not persistent, and sepals, persistent.

*Fragrance*.—None detected.

*Flower buds, before showing petal color*.—Length: About 1.2 cm. Diameter: About 3.5 mm. Shape: Oblong, elongate. Texture and luster: Pubescent; slightly glossy. Color, developing sepals: Close to 144A; sutures, close to N79A.

*Flower diameter*.—About 4 cm.

*Flower depth* (*height*).—About 3.3 cm to 3.6 cm.

*Throat diameter*.—About 1 cm.

*Tube length*.—About 2.4 cm.

*Tube diameter, distally*.—About 9 mm.

*Tube diameter, proximally*.—About 2 mm.

*Petals*.—Quantity and arrangement: Five petals fused in a single salverform whorl. Petal lobe length (from throat): About 2 cm. Petal lobe width: About 2.1 cm. Petal lobe shape: Roughly spatulate. Petal lobe apex: Broadly acute and occasionally shallowly retuse. Petal lobe margin: Entire; moderately undulate. Petal lobe texture and luster, upper surface: Smooth, glabrous; velvety; matte. Petal lobe texture and luster, lower surface: Smooth, glabrous; matte. Throat texture and luster: Smooth, glabrous; slightly glossy. Tube texture and luster: Moderately pubescent; matte. Color: When opening and fully opened, upper surface: Close to 70A to 70B; venation, proximally, close to between N79A and 79A, and distally, close to between 71A to 72A; color becoming closer to 70B with subsequent development. When opening and fully opened, lower surface: Close to between N75A and 75A; venation, close to between 71A and 72A; color becoming closer to N75B to N75C with subsequent development. Flower throat (inside): Close to 79A; venation, close to between 79A and N79A. Flower tube (outside): Close to 79A to 79B; venation, close to 79A to 79B.

*Sepals*.—Quantity and arrangement: Five sepals fused in a single star-shaped whorl; sepals flaring outwardly. Calyx length: About 1.7 cm. Calyx diameter: About 2.3 cm. Length: About 1.5 cm to 1.7 cm. Width: About 3 mm to 3.5 mm. Shape: Narrowly lanceolate to linear. Apex: Acute to somewhat rounded. Margin: Entire. Texture and luster, upper and lower surfaces: Moderately pubescent; pubescence, fine; slightly glossy. Color, upper and lower surfaces: Close to 144A.

*Peduncles*.—Length: About 2.2 cm. Width: About 1 mm to 1.5 mm. Strength: Moderately strong; wiry and flexible, not brittle. Angle: About 45° from the stem axis. Texture and luster: Densely pubescent; slightly glossy. Color: Close to 144A.

*Reproductive organs*.—Stamens: Quantity per flower: About five. Filament length: About 1.7 cm to 1.8 cm. Filament color: Proximally, close to 76A, and distally, fading to close to 76D. Anther length: About 1 mm. Anther shape: Bi-lobed. Anther color: Close to 94B. Pollen amount: Moderate. Pollen color: Close to 157A. Pistils: Quantity per flower: One. Pistil length: About 2 cm. Style length: About 1.6 cm to 1.7 cm. Style color: Proximally, close to 144C to 144D, and distally, close to 79A. Stigma diameter: About 1 mm. Stigma shape: Round. Stigma color: Close to 79A. Ovary color: Close to 144A.

*Seeds and fruits*.—To date, seed and fruit development has not been observed on plants of the new *Petunia*.

Pathogen & pest resistance: To date, plants of the new Petunia have not been noted to be resistant to pathogens or pests common to Petunia plants.

Garden performance: Plants of the new Petunia have been observed to have excellent garden performance and have been observed to tolerate rain, wind and temperatures ranging from about 5° C. to about 40° C.

It is claimed:

1. A new and distinct *Petunia* plant named 'WGPETSMVPV25' as herein illustrated and described.

* * * * *